(12) United States Patent
von Hoffmann et al.

(10) Patent No.: US 6,511,481 B2
(45) Date of Patent: Jan. 28, 2003

(54) METHOD AND APPARATUS FOR FIXATION OF PROXIMAL FEMORAL FRACTURES

(75) Inventors: Gerard von Hoffmann, Coto de Caza, CA (US); Victor V. Cachia, San Juan Capistrano, CA (US); Brad S. Culbert, Rancho Santa Margarita, CA (US)

(73) Assignee: Triage Medical, Inc., Irvine, CA (US)

( * ) Notice: Subject to any disclaimer, the term of this patent is extended or adjusted under 35 U.S.C. 154(b) by 0 days.

(21) Appl. No.: 09/822,803

(22) Filed: Mar. 30, 2001

(65) Prior Publication Data

US 2002/0143333 A1 Oct. 3, 2002

(51) Int. Cl.⁷ .............................................. A61B 17/84
(52) U.S. Cl. ........................................ 606/67; 606/60
(58) Field of Search ............................... 606/60, 65–67, 606/72, 73

(56) References Cited

U.S. PATENT DOCUMENTS

| | | |
|---|---|---|
| 2,077,804 A | 4/1937 | Morrison |
| 2,485,531 A | 10/1949 | Dzus et al. |
| 2,489,870 A | 11/1949 | Dzus |
| 3,489,143 A | 1/1970 | Halloran |
| 4,052,988 A | 10/1977 | Doddi et al. |
| 4,175,555 A | 11/1979 | Herbert |
| 4,275,717 A | 6/1981 | Bolesky |
| 4,463,753 A | 8/1984 | Gustilo |
| 4,640,271 A | 2/1987 | Lower |
| 4,667,663 A | 5/1987 | Miyata |
| 4,688,561 A | 8/1987 | Reese |
| 4,743,257 A | 5/1988 | Tormala et al. |
| 4,790,304 A | 12/1988 | Rosenberg |
| 4,796,612 A | 1/1989 | Reese |
| 4,827,917 A | 5/1989 | Brumfield |
| 4,873,976 A | 10/1989 | Schreiber |
| 4,898,186 A | 2/1990 | Ikada et al. |

(List continued on next page.)

FOREIGN PATENT DOCUMENTS

| | | |
|---|---|---|
| EP | 0525352 A1 | 2/1993 |
| EP | 1 046 376 A1 | 10/2000 |
| FR | 2 699 065 | 12/1992 |
| FR | 2 728 778 | 12/1994 |
| FR | 2 745 709 | 3/1996 |
| FR | 2 800 601 | 11/1999 |
| FR | 2 801 189 | 11/1999 |
| FR | 2 808 182 | 4/2000 |
| GB | 2157788 A | 10/1985 |
| GB | 2173565 A | 10/1986 |
| JP | 64-52439 | 2/1989 |
| WO | WO 91/09572 | 12/1989 |

OTHER PUBLICATIONS

International Search Report, Jun. 10, 2002.

Primary Examiner—Kevin Shaver
Assistant Examiner—Michael B. Priddy
(74) Attorney, Agent, or Firm—Knobbe, Martens, Olson & Bear, LLP

(57) ABSTRACT

Disclosed is a femoral neck fracture fixation device, for reducing and compressing fractures in the proximal femur. The fixation device includes an elongate body with a helical cancellous bone anchor on a distal end. An axially moveable proximal anchor is carried by the proximal end of the fixation device. The device is rotated into position across the femoral neck and into the femoral head, and the proximal anchor is distally advanced to lock the device into place.

80 Claims, 14 Drawing Sheets

U.S. PATENT DOCUMENTS

| | | |
|---|---|---|
| 4,903,692 A | 2/1990 | Reese |
| 4,917,554 A | 4/1990 | Bronn |
| 4,940,467 A * | 7/1990 | Tronzo .................. 606/66 |
| 4,968,317 A | 11/1990 | Tormala et al. |
| 4,978,349 A | 12/1990 | Frigg |
| 5,059,193 A | 10/1991 | Kuslich |
| 5,062,849 A | 11/1991 | Schelhas |
| 5,092,891 A | 3/1992 | Kummer et al. |
| 5,098,433 A | 3/1992 | Freedland |
| 5,122,141 A | 6/1992 | Simpson et al. |
| 5,167,663 A | 12/1992 | Brumfield |
| 5,167,664 A | 12/1992 | Hodorek |
| 5,217,462 A | 6/1993 | Asnis et al. |
| 5,242,447 A | 9/1993 | Borzone |
| 5,246,441 A | 9/1993 | Ross et al. |
| 5,250,049 A | 10/1993 | Michael |
| 5,300,074 A | 4/1994 | Frigg |
| 5,364,398 A | 11/1994 | Chapman et al. |
| 5,370,646 A | 12/1994 | Reese et al. |
| 5,449,359 A | 9/1995 | Groiso |
| 5,452,748 A | 9/1995 | Simmons et al. |
| 5,498,265 A | 3/1996 | Asnis et al. |
| 5,501,695 A | 3/1996 | Anspach, Jr. et al. |
| 5,536,127 A | 7/1996 | Pennig |
| 5,549,610 A | 8/1996 | Russell et al. |
| 5,626,613 A | 5/1997 | Schmieding |
| 5,628,751 A | 5/1997 | Sander et al. |
| 5,662,683 A | 9/1997 | Kay |
| 5,713,903 A | 2/1998 | Sander et al. |
| 5,720,753 A | 2/1998 | Sander et al. |
| 5,725,541 A | 3/1998 | Anspach, III et al. |
| 5,728,097 A | 3/1998 | Mathews |
| 5,728,116 A | 3/1998 | Rosenman |
| 5,741,282 A | 4/1998 | Anspach, III et al. |
| 5,772,662 A | 6/1998 | Chapman et al. |
| 5,849,004 A | 12/1998 | Bramlet |
| 5,871,485 A | 2/1999 | Rao et al. |
| 5,893,850 A | 4/1999 | Cachia |
| 5,904,696 A | 5/1999 | Rosenman |
| 5,908,422 A | 6/1999 | Bresina |
| 5,928,235 A | 7/1999 | Friedl |
| 5,928,244 A | 7/1999 | Tovey et al. |
| 5,935,129 A | 8/1999 | McDevitt et al. |
| 5,947,999 A | 9/1999 | Groiso |
| 5,948,000 A | 9/1999 | Larsen et al. |
| 5,957,924 A | 9/1999 | Tormala et al. |
| 5,968,044 A | 10/1999 | Nicholson et al. |
| 5,976,139 A | 11/1999 | Bramlet |
| 5,984,927 A | 11/1999 | Wenstrom, Jr. et al. |
| 5,984,966 A | 11/1999 | Kiema et al. |
| 5,989,255 A | 11/1999 | Pepper et al. |
| 5,993,459 A | 11/1999 | Larsen et al. |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke et al. |
| 6,007,566 A | 12/1999 | Wenstrom, Jr. |
| 6,007,580 A | 12/1999 | Lehto et al. |
| 6,010,513 A | 1/2000 | Tormala et al. |
| 6,015,410 A | 1/2000 | Tormala et al. |
| 6,019,762 A | 2/2000 | Cole |
| 6,036,701 A | 3/2000 | Rosenman |
| 6,068,648 A | 5/2000 | Cole et al. |
| 6,083,244 A | 7/2000 | Lubbers et al. |
| 6,126,661 A | 10/2000 | Faccioli et al. |
| 6,168,595 B1 | 1/2001 | Durham et al. |
| 6,183,472 B1 * | 2/2001 | Lutz .................. 606/61 |
| 6,183,474 B1 | 2/2001 | Bramlet et al. |
| 6,319,254 B1 | 11/2001 | Giet et al. |

* cited by examiner

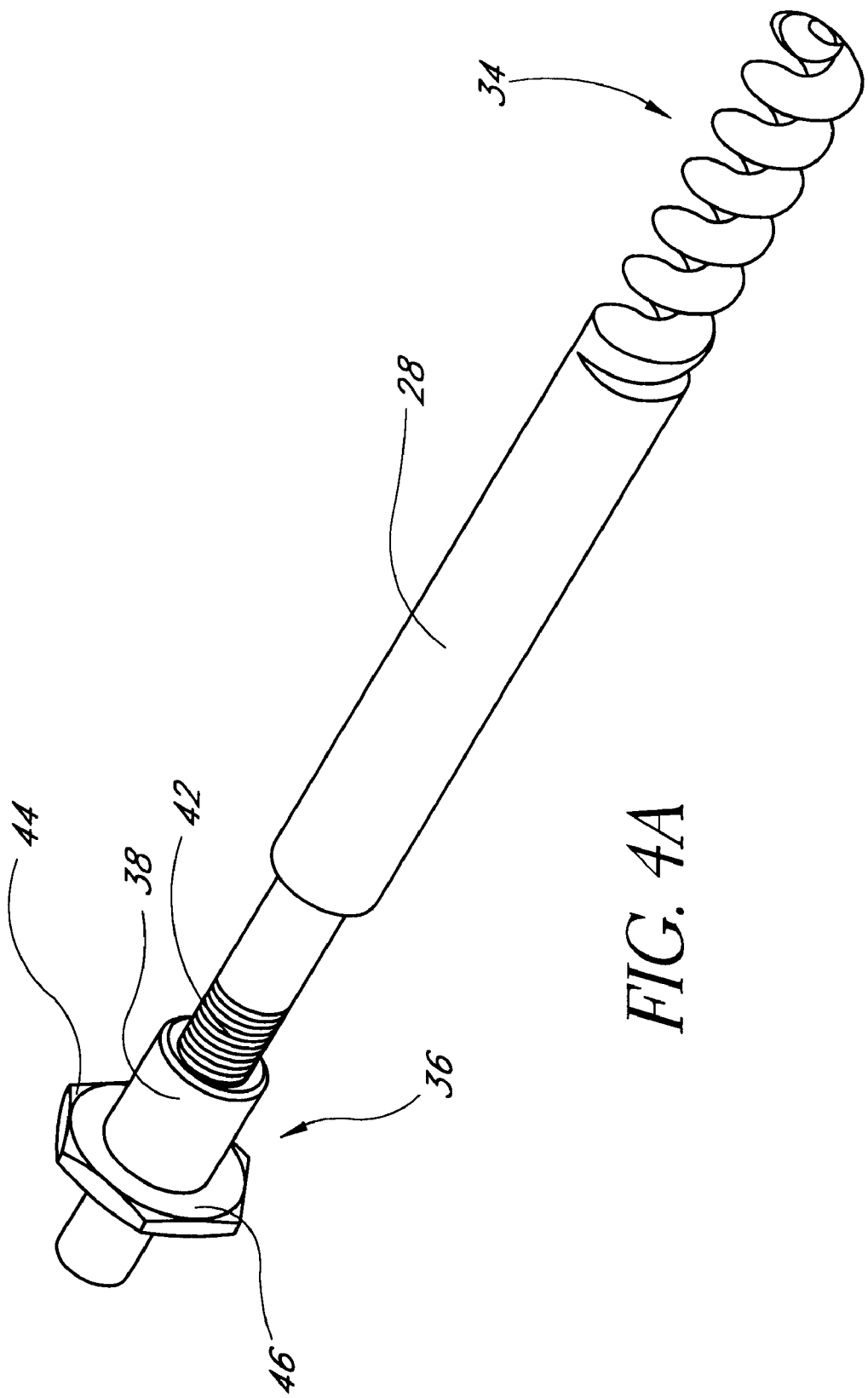

METHOD AND APPARATUS FOR FIXATION OF PROXIMAL FEMORAL FRACTURES

BACKGROUND OF THE INVENTION

The present invention relates to internal bone fracture fixation devices. In one application, the present invention relates to bone fracture fixation devices and methods adapted for fixation of femoral neck and other proximal femoral fractures.

The femur, otherwise known as the thigh bone, generally comprises an elongate shaft extending from the hip to the knee. The proximal end of the shaft includes a head, a neck, a greater trochanter and a lesser trochanter. The head of the femur fits into the acetabular cup of the hip bone to form a ball and socket joint at the hip. The distal end of the femur includes a medial condyle and a lateral condyle. The condyles engage an upper end of the tibia to form the knee joint. Overall, the femur is the longest and strongest bone in the skeleton. However, portions of the femur are extremely susceptible to fracturing.

Pertrochanteric fractures among geriatric patients are the most frequent in connection with those of the region of the neck of the bone. The advanced age and the pathologies which are encountered in these patients make a timely stabilization of skeletal injuries necessary in order to reduce to a minimum the bed confinement and the rehabilitation times. Preferably, devices and procedures are utilized which minimize complications brought about by the so-called immobilization syndrome, which may be lethal for patients in delicate metabolical circumstances. It is also preferable to reduce to a minimum blood losses related to surgical intervention. At the same time, the syntheses means utilized must be stable in order to allow the patient to very timely assume a seated position and, two or three days following the intervention, to reassume an erect posture with progressive bearing of weight.

Internal fixation of femoral fractures in general is one of the most common orthopedic surgical procedures. Fractures of the femur occur in both the proximal portion of the femur and the distal portion of the femur. Fractures of the proximal portion of the femur (hip fractures) are generally classified as femoral neck fractures, intertrochanteric fractures and subtrochanteric fractures. Fractures of the distal portion of the femur (knee fractures) are referred to as supracondylar fractures. Supracondylar fractures generally extend vertically between the condyles at the lower end of the femur to separate the distal portion of the femur into two main bone fragments. A fracture line may be further comminuted to create a plurality of smaller bone fragments. Fractures of the femur which extend into the neck of the bone are generally more difficult to treat than fractures restricted to the shaft of the femur.

Operative treatment of the fractures requires that the fractures be internally fixed and possibly compressed. Fractures of the neck, head or trochanters of the femur have been treated with a variety of compression screw assemblies which include generally a compressionplate having a barrel member, a lag screw and a compressing screw. The compression plate is secured to the exterior of the femur and the barrel member is inserted into a predrilled hole in the direction of the femoral head. The lag screw which has a threaded end and a smooth portion is inserted through the barrel member so that it extends across the break and into the femoral head. The threaded portion engages the femoral head. The compressing screw connects the lag screw to the plate. By adjusting the tension of the compressing screw the compression (reduction) of the fracture can be adjusted.

A variety of elongated implants (nail, screw, pin, etc.) have been developed, which are adapted to be positioned along the longitudinal axis of the femoral neck with a leading (distal) end portion in the femoral head so as to stabilize a fracture of the femoral neck. The elongated implant may be implanted by itself or connected to another implant such as a side plate or intramedullary rod. The leading end portion of the, implant typically includes means to positively grip the femoral head bone (external threads, expanding arms, etc.), but the inclusion of such gripping means can introduce several significant problems. First, implants with sharp edges on the leading end portion, such as the externally threaded implants, exhibit a tendency to migrate proximally towards the hip joint bearing surface after implantation. This can occur when the proximal cortical bone has insufficient integrity to resist distal movement of the screw head. Such proximal migration under physiological loading, which is also referred to as femoral head cut-out, can lead to significant damage to the adjacent hip joint. Also, the externally threaded implants can generate large stress concentrations in the bone during implantation which can lead to stripping of the threads formed in the bone and thus a weakened grip. The movable arms of known expanding arm devices are usually free at one end and attached at the other end to the main body of the leading end portion of the implant. As a result, all fatigue loading is concentrated at the attached ends of the arms and undesirably large bending moments are realized at the points of attachment. In addition, conventional threaded implants generally exhibit insufficient holding power under tension, such that the threads can be stripped out of the femoral head either by overtightening during the implantation procedure or during post operative loading by the patient's weight.

Thus, notwithstanding the variety of efforts in the prior art, there remains a need for a femoral neck fixation device with improved locking force within the femoral head, which resists migration and rotation, and which can be easily and rapidly deployed within the femur.

SUMMARY OF THE INVENTION

There is provided in accordance with one aspect of the present invention, a method of securing a first bone fragment to a second bone fragment. The method comprises the steps of drilling a bore through the first bone fragment in the direction of the second bone fragment, and advancing a fixation device through the bore. At least a first portion of the fixation device is rotated to secure the fixation device to the second fragment, and a second portion of the fixation device is axially advanced to engage the first fragment.

In one application of the method, the second bone fragment comprises the head of a femur. Alternatively, the second bone fragment comprises the tibia, the fibula, or the femur. The first bone fragment may alternatively comprise a condyle.

The method may additionally comprise the step of positioning a plate adjacent the first bone fragment and advancing the fixation device through the plate.

In accordance with another aspect of the present invention, there is provided a femoral neck fracture fixation device. The device comprises an elongated body, having a proximal end and a distal end. A helical distal anchor is provided on the distal end. A first retention structure is provided on the body, proximal to the distal anchor, and a proximal anchor surface is moveably carried by the body.

The proximal anchor surface is moveable in the distal direction with respect to the body, and the retention structure resists proximal movement of the proximal anchor surface with respect to the body.

In one embodiment, the first retention structure comprises an annular structure such as one or more flanges or threads. The proximal anchor surface may be carried by a tubular sleeve, for axially moveably receiving the elongate body. A second retention structure is preferably provided on the interior of the tubular sleeve for cooperating with the first retention structure on the body.

In accordance with a further aspect of the present invention, there is provided a bone fracture fixation device. The fixation device comprises an elongate body having a proximal end and a distal end. A cancellous bone anchor is carried by the distal end. A proximal anchor is axially moveably carried on the body, and a complementary surface structure is in, between the body and the proximal anchor to permit advancing the proximal anchor in the distal direction to tighten the fixation device but resist axial proximal movement of the proximal anchor.

In accordance with another aspect of the present invention, there is provided a method of treating a femoral fracture. The method comprises the steps of drilling a bore distally into the femur in the direction of a fracture, and advancing a fixation device into the bore. The fixation device is rotated to engage bone distal to the fracture, and a proximal anchor is advanced distally along the fixation device to compress the fracture.

Preferably, the drilling step comprises drilling the bore along an axis which extends through the femoral neck and in the direction of the head of the femur. In one embodiment, the advancing a proximal anchor step comprises axially advancing the proximal anchor without rotating the proximal anchor with respect to the fixation device. The femoral fracture may be a femoral neck fracture, an intertrochanteric fracture or a subtrochanteric fracture.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 4A is a front elevational perspective view of a modified fixation device of the present invention.

DETAILED DESCRIPTION OF THE PREFERRED EMBODIMENT

Figure 1:
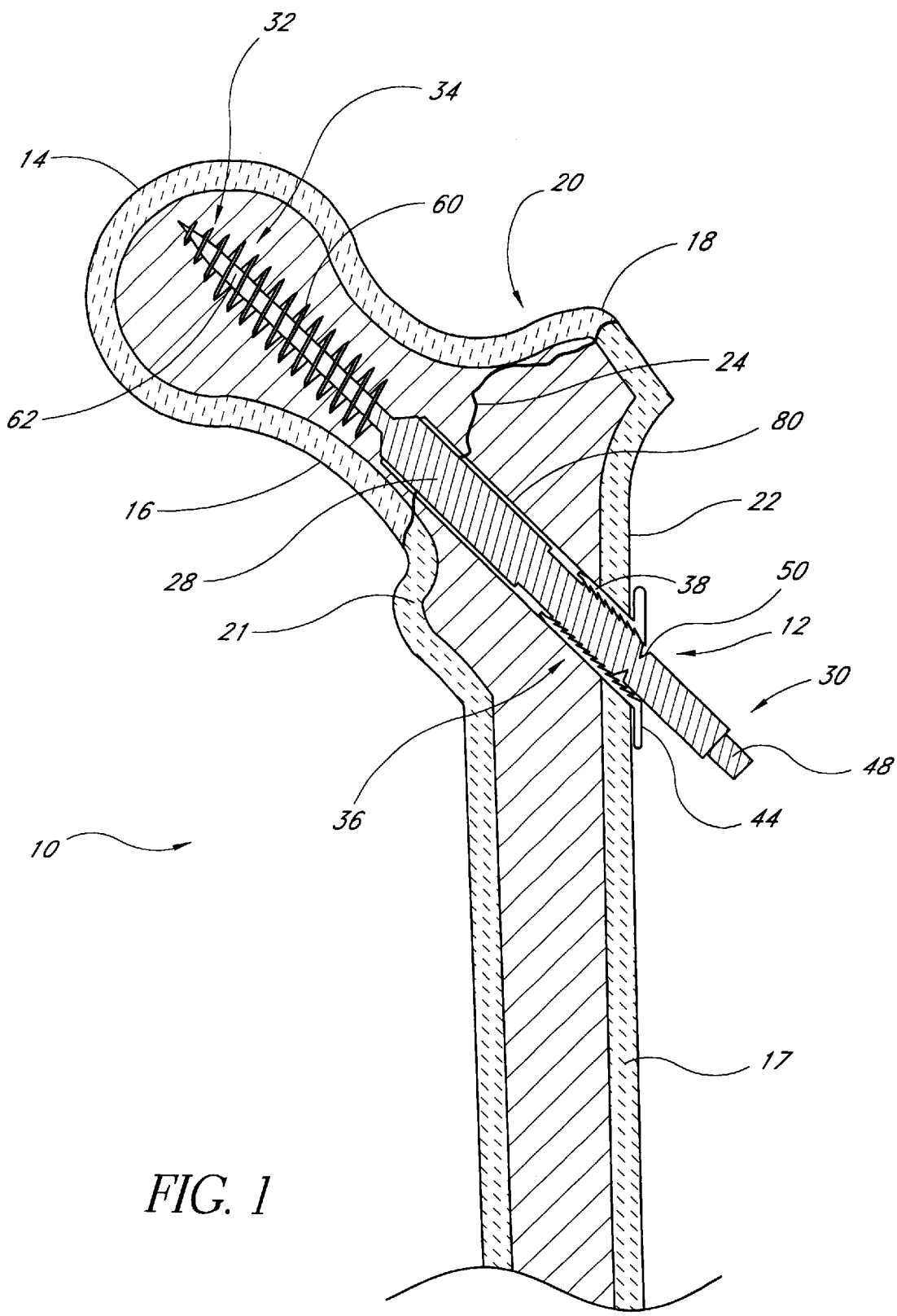
FIG. 1 is a posterior elevational posterior cross section through the proximal portion of the femur, having a femoral neck fracture fixation device positioned therein.

Although the fixation devices of the present invention will be disclosed primarily in the context of fractures of the proximal femur, the methods and structures disclosed herein are intended for application in any of a wide variety of bones and fractures, as will be apparent to those of skill in the art in view of the disclosure herein. For example, the bone fixation device of the present invention is applicable in a wide variety of fractures and osteotomies in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. A wide variety of phalangeal and metatarsal osteotomies and fractures of the foot may also be stabilized using the bone fixation device of the present invention. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. The bone fixation device may be used with or without plate(s) or washer(s), all of which can be either permanent, absorbable, or combinations.

Fractures of the fibular and tibial malleoli, pilon fractures and other fractures of the bones of the leg may be fixated and stabilized with the present invention with or without the use of plates, both absorbable or non-absorbing types, and with alternate embodiments of the current invention. Fractures and osteotomies of the mid and hind foot, tarsal arthrodesis and osteotomy, or others as are known to those with skill in the art. One example is the fixation of the medial malleolar avulsion fragment fixation with the radially and axially expanding compression device.

The fixation device of the present invention may also be used to attach tissue or structure to the bone, such as in ligament reattachment and other soft tissue attachment procedures. Plates and other implants may also be attached to bone, using either resorbable or nonresorbable fixation devices depending upon the implant and procedure. The fixation device may also be used to attach sutures to the bone, such as in any of a variety of tissue suspension procedures.

For example, peripheral applications for the fixation devices include utilization of the device for fastening soft tissue such as capsule, tendon or ligament to bone. It may also be used to attach a synthetic material such as marlex mesh, to bone or allograft material such as tensor fascia lata, to bone. In the process of doing so, retention of the material to bone may be accomplished with the collar as shown, or the pin and or collar may be modified to accept a suture or other material for facilitation of this attachment.

Specific examples include attachment of the posterior tibial tendon to the navicular bone in the Kidner operation. Navicular-cuneiform arthrodesis may be performed utilizing the device and concurrent attachment of the tendon may be accomplished. Attachment of the tendon may be accomplished in the absence of arthrodesis by altering the placement of the implant in the adjacent bone.

Ligament or capsule reattachment after rupture, avulsion or detachment, such as in the ankle, shoulder or knee can also be accomplished using the devices disclosed herein.

The fixation devices may be used in combination with semi tubular, one-third tubular and dynamic compression plates, both of metallic and absorbable composition, if the collar is modified to match the opening on the plate.

The canulated design disclosed below can be fashioned to accept an antibiotic impregnated rod for the slow adsorption of medication locally. This may be beneficial for prophylaxis, especially in open wounds, or when osteomyelitis is present and stabilization of fracture fragments is indicated.

A kit may be assembled for field use by military or sport medical or paramedical personnel. This kit contains an implanting tool, and a variety of implant device size and types. The kit may include additional components such as sterilization or disinfectant materials, a skin stapler, bandages, gloves, and basic tools for emergent wound and fracture treatment. Antibiotic rods would be included for wound prophylaxis during transport.

Referring to FIG. 1, there is illustrated a posterior side elevational view of the proximal portion of a femur, 10, having a fixation device 12 positioned therein. The proximal end of the femur 10 comprises a head 14 connected by way of a neck 16 to the long body or shaft 17 of the femur 10. As illustrated in FIG. 1, the neck 16 is smaller in diameter than the head 14. The neck 16 and head 14 also lie on an axis which, on average in humans, crosses the longitudinal axis of the body 17 of the femur 10 at an angle of about 126°. The risk of fracture at the neck 16 is thus elevated, among other things, by the angular departure of the neck 16 from the longitudinal axis of the body 17 of femur 10 and also the reduced diameter of the neck 16 with respect to the head 14.

The greater trochanter 18 extends outwardly above the junction of the neck 16 and the body 17 of the femur 10. On the medial side of the greater trochanter 18 is the. trochanteric fossa 20. This depression accommodates the insertion of the obturator externus muscle. The lesser trochanter 21 is located posteromedially at the junction of the neck 16 and the body 17 of the femur 10. Both the greater trochanter 18 and the lesser trochanter 21 serve for the attachment of muscles. On the posterior surface of the femur 10 at about the same axial level as the lesser trochanter 21 is the gluteal tuberosity 22, for the insertion of the gluteus maximus muscle. Additional details of the femur are well understood in the art and not discussed in further detail herein.

FIG. 1 illustrates a fracture 24 which crosses the femur approximately in the area of the greater trochanter 18. Fractures of the proximal portion of the femur 10 are generally classified as femoral neck fractures, intertrochanteric fractures and subtrochanteric fractures. All of these fractures will be deemed femoral neck fractures for the purpose of describing the present invention.

Referring to FIGS. 1 and 3, the fixation device 12 comprises a body 28 extending between a proximal end 30 and a distal end 32. The length, diameter and construction materials of the body 28 can be varied, depending upon the intended clinical application. In an embodiment optimized for femoral neck fractures in an adult human population, the body 28 will generally be within the range of from about 45 mm to about 120 mm in length after sizing, and within the range of from about 3 mm to about 8 mm in maximum diameter. The major diameter of the helical anchor, discussed below, may be within the range of from about 6 mm to about 12 mm. In general, the appropriate dimensions of the body 28 will vary, depending upon the specific fracture. In rough terms, for a malleolar fracture, shaft diameters in the range of from about 3 mm to about 4.5 mm may be used, and lengths within the range of from about 25 mm to about 70 mm. For condylar fractures, shaft diameters within the range of from about 4 mm to about 6.5 mm may be used with lengths within the range of from about 25 mm to about 70 mm. For colles fractures (distal radius and ulna), diameters within the range of from about 2.5 mm to about 3.5 mm may be used with any of a variety of lengths within the range of from about 6 mm to about 120 mm.

In one embodiment, the body 28 comprises titanium. However, as will be described in more detail below, other metals or bioabsorbable or nonabsorbable polymeric materials may be utilized, depending upon the dimensions and desired structural integrity of the finished fixation device 12.

The distal end 32 of the body 28 is provided with a cancellous bone anchor or distal anchor 34. Additional details of the cancellous bone anchor are described below. In general, the cancellous bone anchor 34 is adapted to be rotationally inserted into the cancellous bone within the head 14 of the femur 10, to retain the fixation device 12 within the femoral head.

The proximal end 30 of the body 28 is provided with a proximal anchor 36. Proximal anchor 36 is axially distally moveable along the body 28, to permit compression of the fracture 24 as will be apparent from FIG. 1. Complimentary locking structures such as threads or ratchet like structures between the proximal anchor 36 and the body 28 resist proximal movement of the anchor 36 with respect to the body 28 under normal use conditions. The proximal anchor 36 can be axially advanced along the body 28 either with or without rotation, depending upon the complementary locking structures as will be apparent from the disclosure herein.

In the illustrated embodiment, proximal anchor 36 comprises a housing 38 such as a tubular body, for coaxial movement along the body 28. The housing 38 is provided with one or more surface structures 40 such as radially inwardly projecting teeth or flanges, for cooperating with complementary surface structures 42 on the body 28. The surface structures 40 and complementary surface structures 42 permit distal axial travel of the proximal anchor 36 with respect to the body 28, but resist proximal travel of the proximal anchor 36 with respect to the body 28. Any of a variety of complementary surface structures which permit one way ratchet like movement may be utilized, such as a plurality of annular rings or helical threads, ramped ratchet structures and the like for cooperating with an opposing ramped structure or pawl.

Retention structures 42 are spaced axially apart along the body 28, between a proximal limit 54 and a distal limit 56. The axial distance between proximal limit 54 and distal limit 56 is related to the desired axial range of travel of the proximal anchor 36, and thus the range of functional sizes of the fixation device 12. In one embodiment of the fixation device 12, the retention structure 42 comprise a plurality of threads, adapted to cooperate with the retention structures 40 on the proximal anchor 36, which may be a complementary plurality of threads. In this embodiment, the proximal anchor 36 may be distally advanced along the body 28 by rotation of the proximal anchor 36 with respect to the body 28. Proximal anchor 36 may be advantageously removed from the body 28 by reverse rotation, such as to permit removal of the body 28 from the patient. In this embodiment, a flange 44 is preferably provided with a gripping structure to permit a removal tool to rotate the flange 44 with respect to the body 28. Any of a variety of gripping structures may be provided, such as one or more slots, flats, bores or the like. In one embodiment, the flange 44 is provided with a polygonal, and, in particular, a pentagonal or hexagonal circumference.

The flange 44 seats against the outer surface of the femur or tissue adjacent the femur. The flange 44 is preferably an annular flange, to optimize the footprint or contact surface area between the flange 44 and the femur. Circular or polygonal shaped flanges for use in femoral head fixation will generally have a diameter of at least about 4 mm greater than the adjacent body 28 and often within the range of from about 4 mm to about 20 mm or more greater than the adjacent body 28. In a modified embodiment, the flange 44 can be curved to match the curved shape of the femur and further optimize the footprint or contact surface area between the flange 44 and the femur.

Tensioning and release of the proximal anchor 36 may be accomplished in a variety of ways, depending upon the intended installation and removal technique. For example, a simple threaded relationship between the proximal anchor 36 and body 28 enables the proximal anchor 36 to be rotationally tightened as well as removed. However, depending upon the axial length of the threaded portion on the pin 28, an undesirably large amount of time may be required to rotate the proximal anchor 36 into place. For this purpose, the locking structures on the proximal anchor 36 may be adapted to elastically deform or otherwise permit the proximal anchor 36 to be distally advanced along the body 28 without rotation, during the tensioning step. The proximal anchor 36 may be removed by rotation as has been discussed. In addition, any of a variety of quick release and quick engagement structures may be utilized. For example, the threads or other retention structures surrounding the body 28 may be interrupted by two or more opposing flats. Two or more corresponding flats are provided on the interior of the housing 38 by proper rotational alignment of the housing 38 with respect to the body 28, the housing 38 may be easily distally advanced along the body 28 and then locked to the body 28 such as by a 90° or other partial rotation of the housing 38 with respect to the body 28. Other rapid release and rapid engagement structures may also be devised, and still accomplish the advantages of the present invention.

Figure 2:
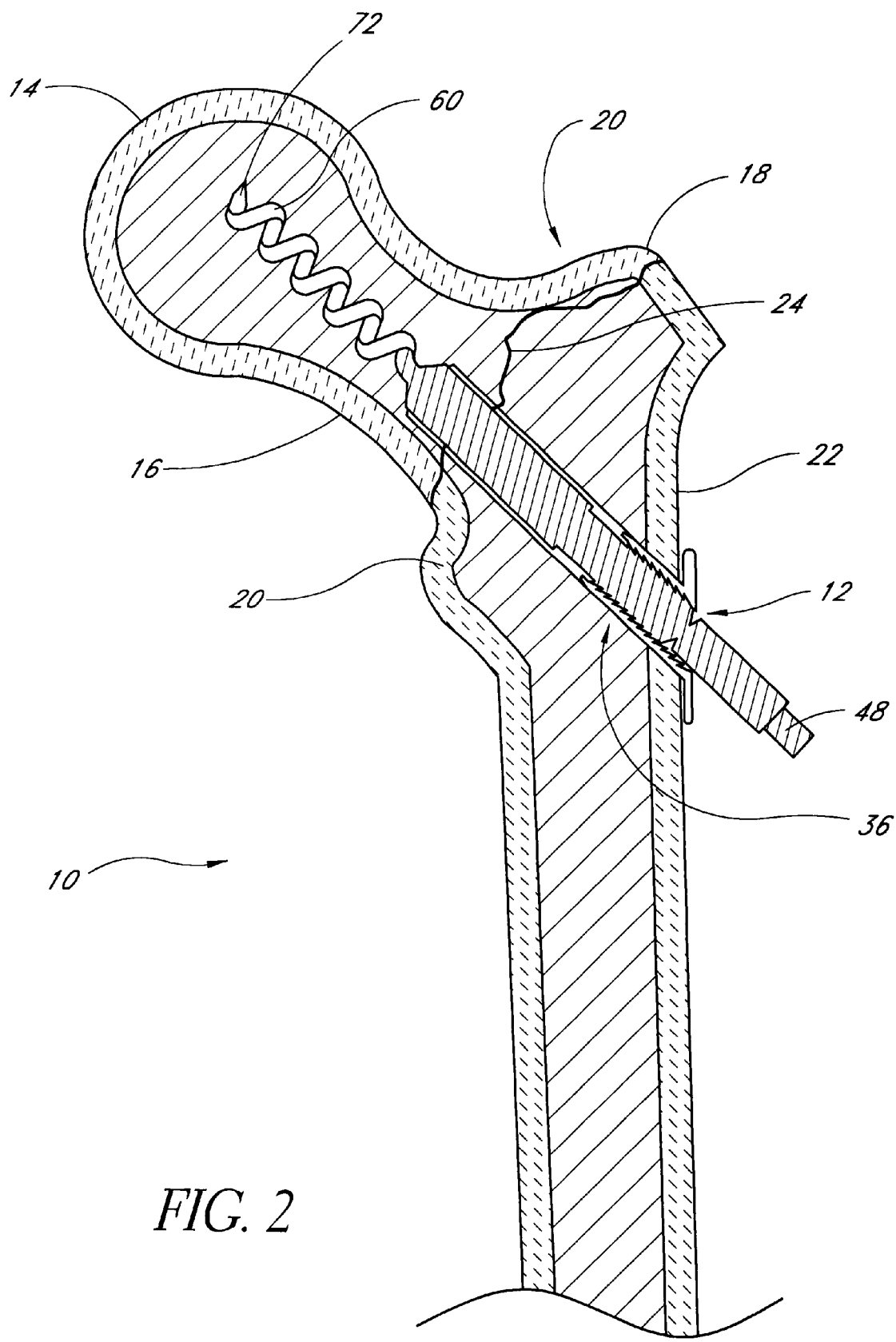
FIG. 2 is a posterior cross section as in FIG. 1, with a modified fixation device positioned therein.
Figure 3A:
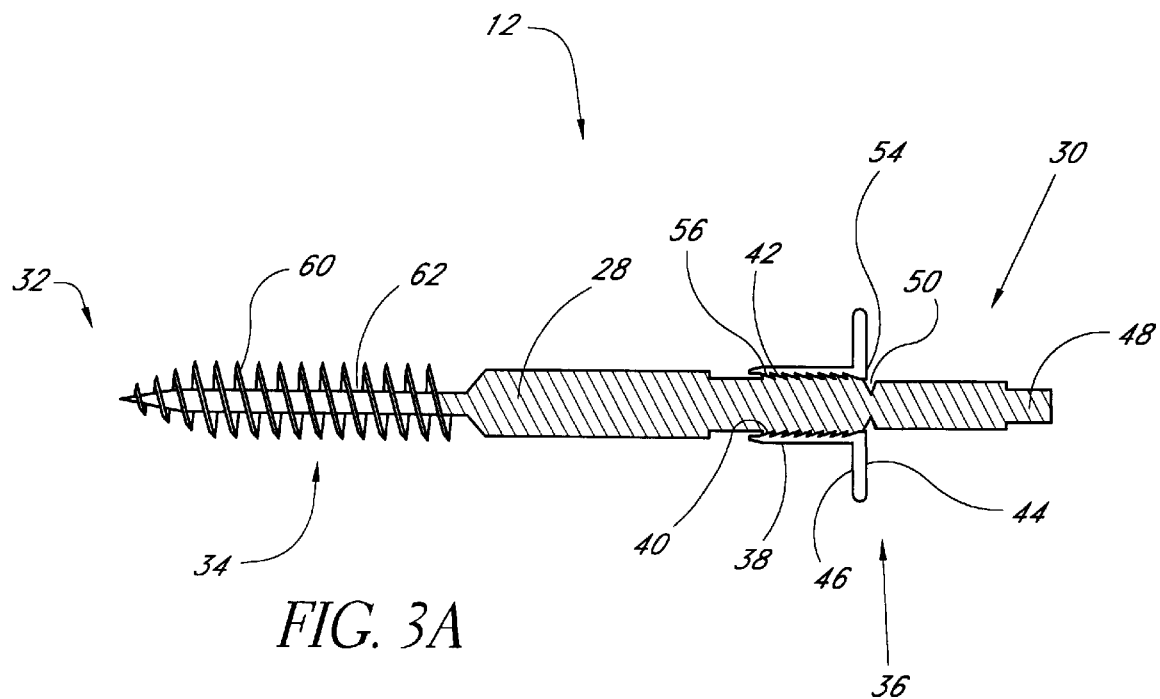
FIG. 3A is a side elevational cross section of a fixation device similar to that of FIG. 1.
Figure 3B:
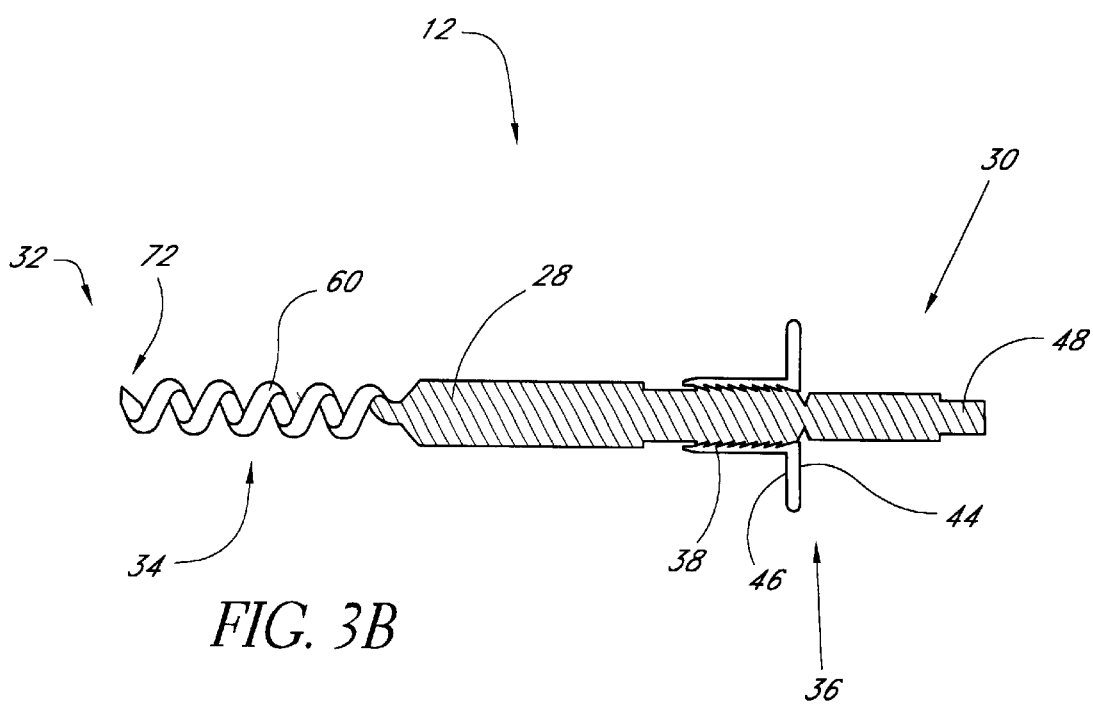
FIG. 3B is a side elevational cross section of a fixation device similar to that of FIG. 2.

In the embodiments illustrated in FIGS. 1 and 2, the bone contacting surface 46 of the flange 44 resides in or approximately on a plane which is inclined with respect to the longitudinal axis of the body 28. Any of a variety of angular relationships between the bone contacting surface 46 of the flange 44 and the longitudinal axis of the body 28 and housing 38 may be utilized, depending upon the anticipated entrance angle of the body 28 and associated entrance point surface of the femur 10. In general, the longitudinal axis extending through the head 14 and neck 16 of the human femur is inclined at an angle of approximately 126° from the longitudinal axis of the long body 17 of the femur 10. Angles between the longitudinal axis of body 28 and tissue contacting surface 46 within the range of from about 90° to about 140° will generally be utilized, often within the range of from about 100° to about 120°, for fixed angle fixation devices. Perpendicular flanges (i.e., 90°) are illustrated in FIGS. 3A and 3B.

The clinician can be provided an array of proximal anchors 36 of varying angular relationships between the bone contacting surface 46 and the longitudinal axis of the body 28 and housing 38 (e.g., 90°, 100°, 110°, 120°, and 130°). A single body 28 can be associated with the array such as in a single sterile package. The clinician upon identifying the entrance angle of the body 28 and the associated entrance point surface orientation of the femur 10 can choose the anchor 36 from the array with the best fit angular relationship, for use with the body 28.

Figure 9:
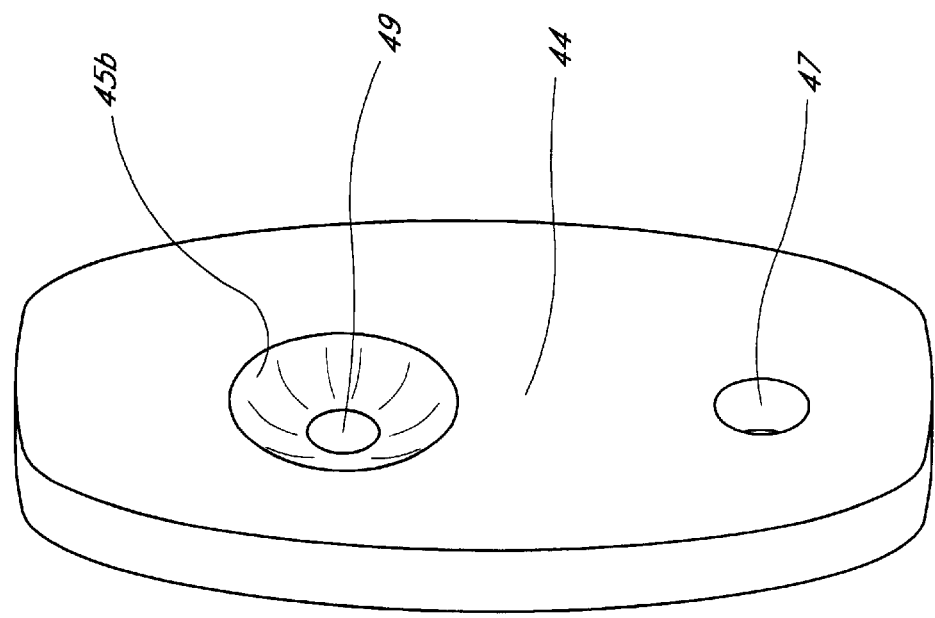
FIG. 9 is a front perspective view of the proximal anchor of FIG. 8.
Figure 8:
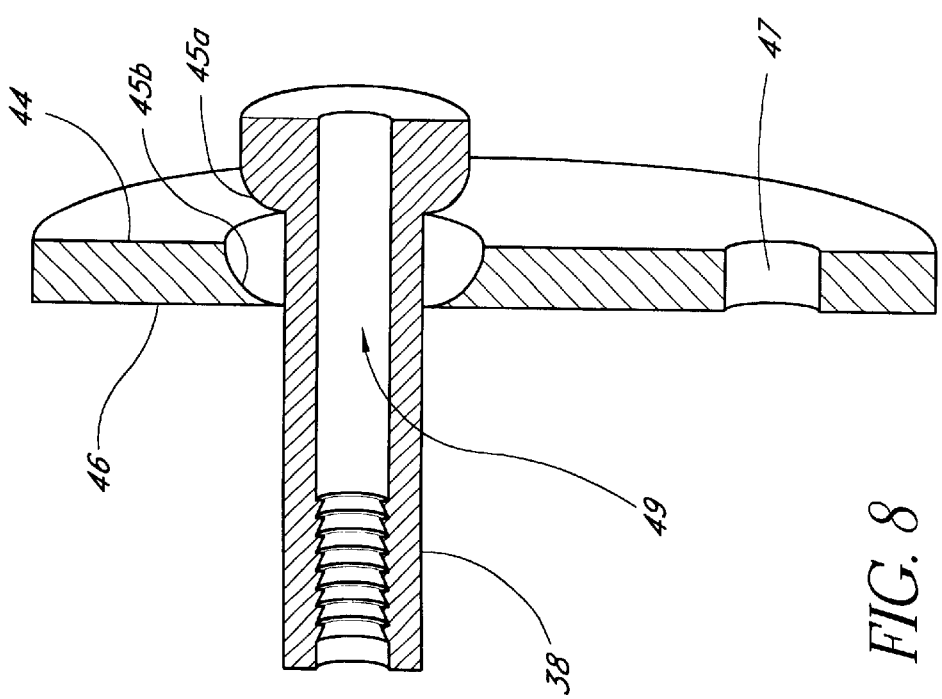
FIG. 8 is a cross sectional view through an angularly adjustable proximal anchor plate.

In accordance with an optional feature, illustrated in FIGS. 8 and 9, the flange 44 is angularly adjustable with respect to the longitudinal axis of the body 28. More specifically, in this embodiment, the tubular housing 38 is a separate component from the flange 44. The housing 38 and the flange 44 preferably include corresponding semi-spherical or radiused surfaces 45a, and 45b. The surface 45b surrounds an aperture 49 in the flange 44. This arrangement allows the housing 38 to extend through and pivot with respect to the flange 44. As such, the angular relationship between the bone contacting surface 46 of the flange 44 and the longitudinal axis of the body 28 can vary in response to the entrance angle.

As an independent feature in FIGS. 8 and 9, the flange 44 is enlarged and includes one or two or more openings 47 for receiving one or two or more femoral shaft screws (not shown). The flange 44 may be elongated anatomically distally parallel to the axis of the femur, so that it functions simultaneously as a plate, as will be discussed in connection with FIG. 6.

With reference back to FIGS. 1 and 2, the proximal end 30 of the body 28 is preferably additionally provided with rotational coupling 48, for allowing the body 28 to be rotationally coupled to a driving device. Any of a variety of driving devices may be utilized, such as electric drills or hand tools which allow the clinician to manually rotate the cancellous bone anchor 34 into the head of the femur. Thus, the rotational coupling 48 may have any of a variety of cross sectional configurations, such as one or more flats or splines.

In one embodiment, the rotational coupling 48 comprises a proximal projection of the body 28 having a polygonal cross section, such as a hexagonal cross section. The rotational coupling 48 is illustrated as a male component, machined or milled or attached to the proximal end 30 of the body 28. However, the rotational coupling may also be in the form of a female element, such as a hexagonal or other noncircular cross sectioned lumen extending throughout a proximal portion or the entire length of the body 28. Although illustrated as solid throughout, the body 28 may be cannulated to accommodate installation over a placement wire as is understood in the art. The cross section of the central cannulation can be made non circular, e.g., hexagonal, to accommodate a corresponding male tool for installation or removal of the device regardless of the location of the proximal break point, as will be discussed.

The body 28 may be provided with at least one and preferably two or three or more break points 50 spaced axially apart along the proximal portion of the body 28. Break points 50 comprise a weakened transverse plane through the body 28, which facilitate severing of the proximal portion of the body 28 following proper tensioning of the proximal anchor 36. Break point 50 may be constructed in any of a variety of ways, such as by machining or milling an annular recess into the exterior wall of the body 28, or created one or more transverse perforations through the body 28 such as by mechanical, laser, or EDM drilling.

In all of the embodiments illustrated herein, the distal anchor 34 comprises a helical locking structure 60 for engaging cancellous bone. The locking structure 60, such as a flange, may either be wrapped around a central core 62 or an axial lumen, as discussed below. The flange extends through at least one and generally from about two to about 50 or more full revolutions depending upon the axial length of the distal anchor and intended application. For most femoral neck fixation devices, the flange will generally complete from about 2 to about 20 revolutions. The helical flange 60 is preferably provided with a pitch and an axial spacing to optimize the retention force within cancellous bone, to optimize compression of the fracture.

The helical flange 60 of the embodiment illustrated in FIG. 1 is shaped generally like a flat blade or radially extended screw thread. However, it should be appreciated that the helical flange 60 can have any of a variety of cross sectional shapes, such as rectangular, triangular or other as deemed desirable for a particular application through routine experimentation in view of the disclosure herein. The outer edge of the helical flange 60 defines an outer boundary. The ratio of the diameter of the outer boundary to the diameter of the central core 62 can be optimized with respect to the desired retention force within the cancellous bone and giving due consideration to the structural integrity and strength of the distal anchor 34. Another aspect of the distal anchor 34 that can be optimized is the shape of the outer boundary and the central core 62, which in the illustrated embodiment are generally cylindrical with a tapered distal end 32.

The distal end 32 and/or the outer edges of the helical flange 60 may be atraumatic (e.g., blunt or soft). This inhibits the tendency of the fixation device 12 to migrate anatomically proximally towards the hip joint bearing surface after implantation (i.e., femoral head cut-out). Distal migration is also inhibited by the dimensions and presence of the proximal anchor 36, which has a larger footprint than conventional screws.

Figure 3C:
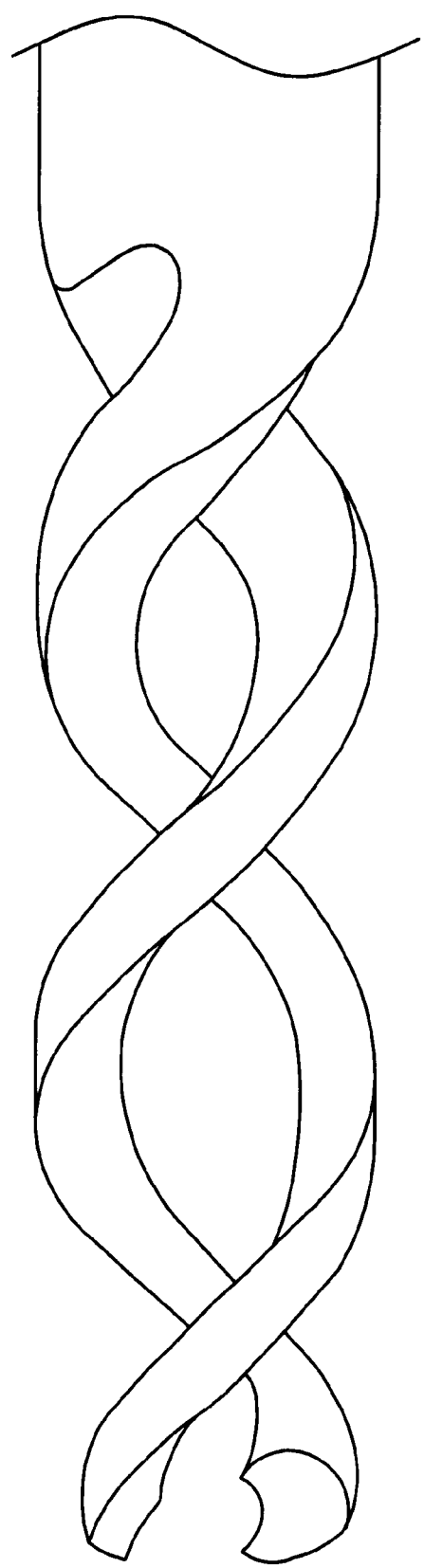
FIG. 3C is a side elevational view of a double helix distal anchor.
Figure 4B:
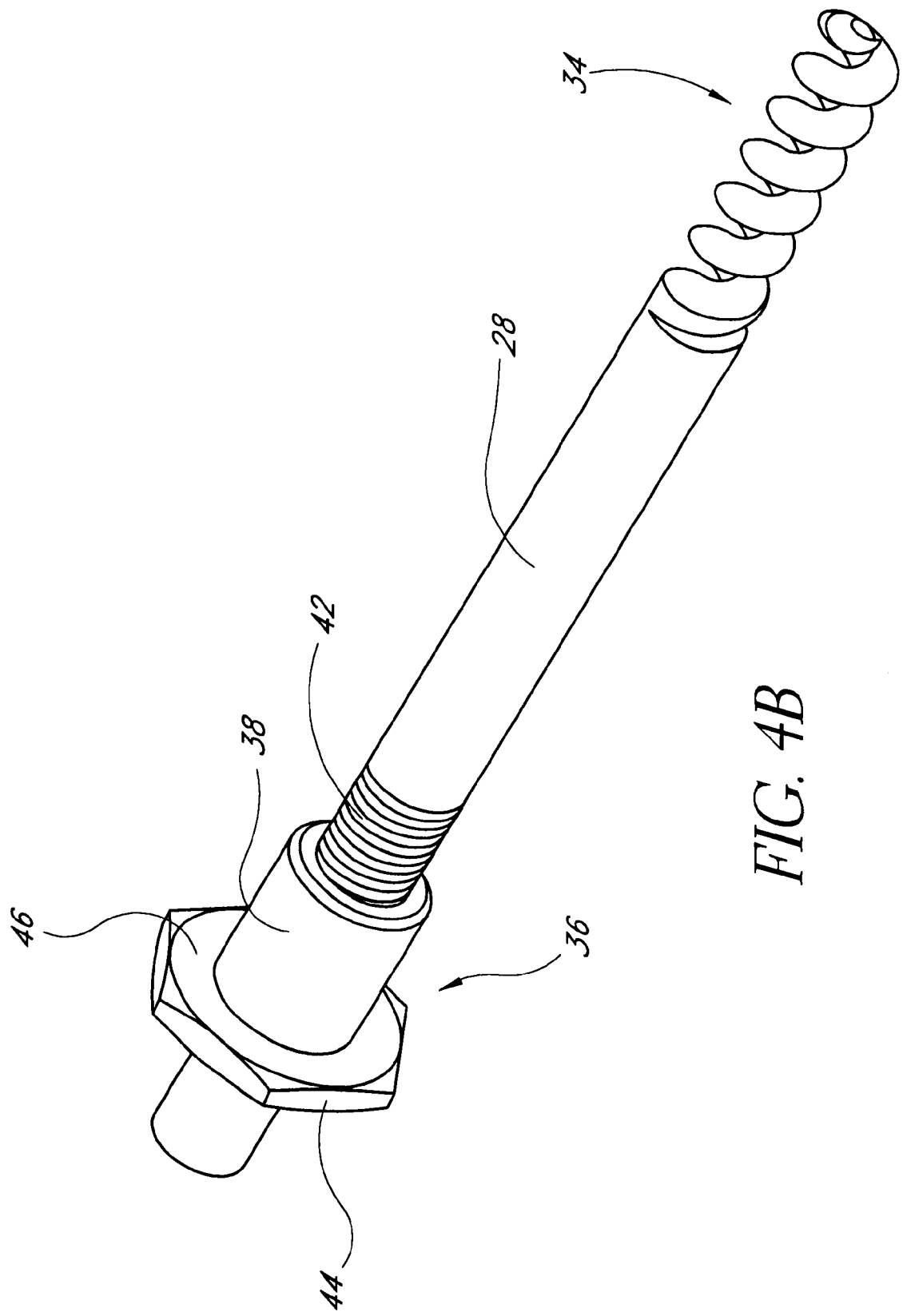
FIG. 4B is a front elevational perspective view of a further modification to the fixation device of the present invention.

Referring to FIGS. 2 and 4, a variation of the distal anchor 34 is illustrated. The distal anchor 34 comprises an elongated helical locking structure 60 that is spirally wrapped about an imaginary cylinder through at least one and preferably from about two to about 20 or more fill revolutions. As with the previous embodiment, the elongated body 60 is provided with a pitch and an axial spacing to optimize the retention force within cancellous bone, which optimizes compression of the fracture. The tip 72 of the elongated body 60 may be pointed. A double helix variation is illustrated in FIG. 3C. The double helix anchor may be incorporated into any of the designs disclosed elsewhere herein.

Figure 5:
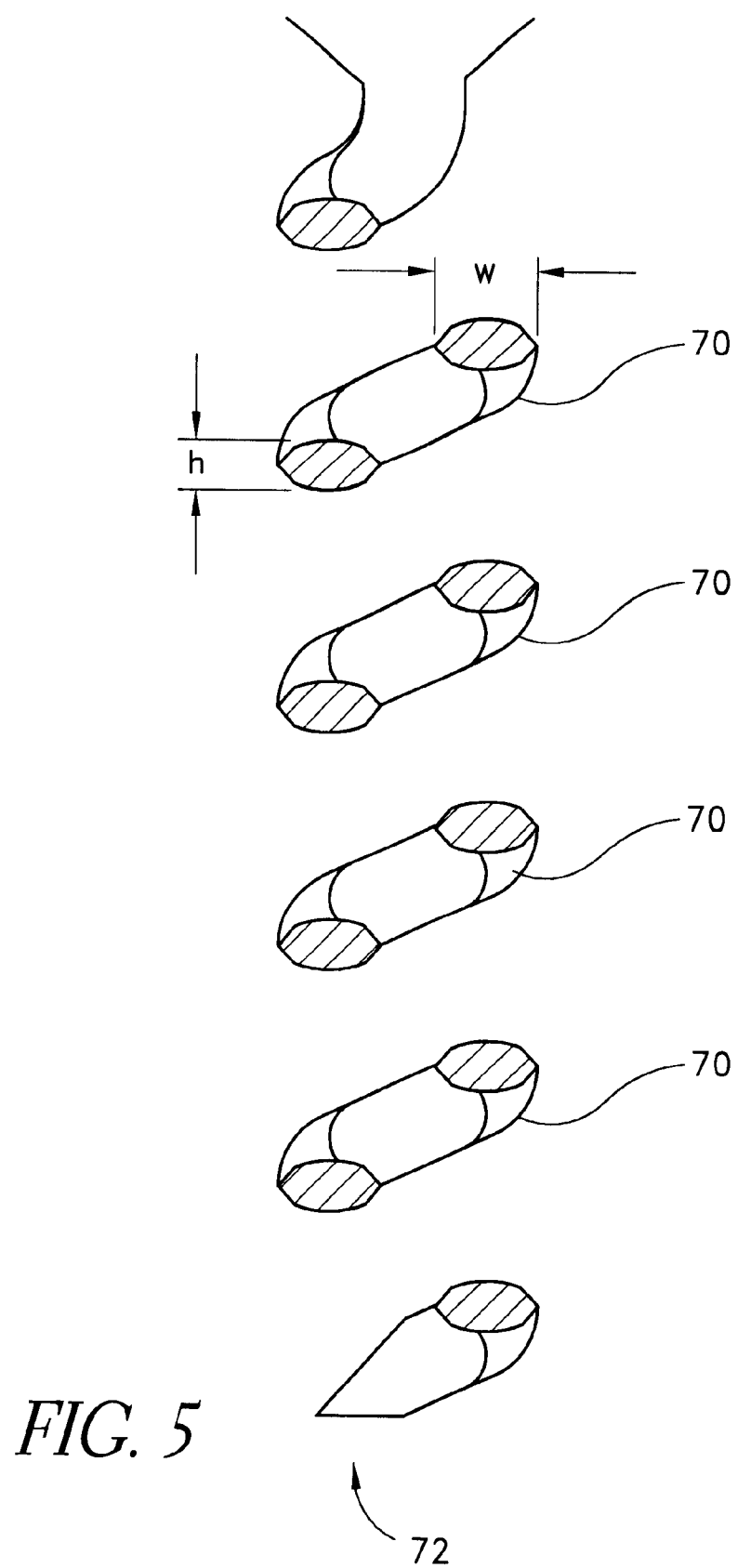
FIG. 5 is an axial cross sectional view through a distal end of a fixation device of the present invention.

FIG. 5 is an axial cross sectional view through a distal anchor of the type illustrated in FIGS. 2 and 4. FIG. 5 also illustrates the cross-section of the helical flange which forms the spiral locking structure. The cross-section has a width w, and a height h. Through routine experimentation, the shape, the width w and height h of the elongated body can be varied to optimize the retention force within cancellous bone. When w is approximately equal to h, the cross section can be circular, square or faceted. In general, w and h are within the range of from about 1 mm to about 8 mm for use in the femoral neck application.

In any of the embodiments herein, an antirotation lock may be provided between the distal anchor and the proximal collar or plate, such as a spline or other interfit structure to prevent relative rotation of the proximal and distal ends of the device following implantation.

In use, the clinician first identifies a patient having a femoral neck fracture, which is fixable by an internal fixation device. The clinician accesses the proximal femur, reduces the fracture if necessary and selects a bone drill and drills a hole 80 in accordance with conventional techniques. Preferably, the hole 80 has a diameter within the range from about 3 mm to about 8 mm. This diameter may be slightly larger than the diameter of the distal anchor 34. The hole 80 preferably extends up to or slightly beyond the fracture 24.

A fixation device 12 having an axial length and outside diameter suitable for the through hole 80 is selected. The distal end 32 of the fixation device 12 is advanced distally into the hole 80 until the distal anchor 34 reaches the distal end of the hole 80. The proximal anchor 36 may be carried by the fixation device 12 prior to advancing the body 28 into the hole 80, or may be attached following placement of the body 28 within the hole 80. Once the body 28 is in place, the clinician may use any of a variety of driving devices, such as electric drills or hand tools to rotate the cancellous bone anchor 34 into the head of the femur.

While proximal traction is applied to the proximal end 30 of body 28, such as by conventional hemostats, pliers or a calibrated loading device, the proximal anchor 36 is advanced distally until the anchor 36 fits snugly against the outer surface of the femur or tissue adjacent the femur. Appropriate tensioning of the fixation device 12 is accomplished by tactile feedback or through the use of a calibration device for applying a predetermined load on the implantation device. One advantage of the structure of the present invention is the ability to adjust compression independently of the setting of the distal anchor 34.

Following appropriate tensioning of the proximal anchor 36, the proximal extension 30 of the body 28 is preferably cut off or snapped off and removed. Body 28 may be cut using conventional saws, cutters or bone forceps which are routinely available in the clinical setting. Alternatively, the fixation device can be selected such that it is sized to length upon tensioning, so no proximal projection remains.

Following trimming the proximal end 30 of body 28, the access site may be closed and dressed in accordance with conventional wound closure techniques.

Preferably, the clinician will have access to an array of fixation devices 12, having, for example, different diameters, axial lengths and angular relationships. These may be packaged one per package in sterile envelopes or peelable pouches, or in dispensing cartridges which may each hold a plurality of devices 12. Upon encountering a fracture for which the use of a fixation device is deemed appropriate, the clinician will assess the dimensions and load requirements, and select a fixation device from the array which meets the desired specifications.

In some instances, a clinician may want to introduce two or more fixation devices 12 into the femoral head 14 to secure the fracture 24. This may be desirable if the clinician determines that, based upon the nature of the fracture 24, there is a possibility that the head 14 of the femur 10 could rotate about a single fixation device 12. Even minor rotation can inhibit the healing of the fracture. Significant rotation can result in failure of the fixation device or necrosis of the femoral head. Two fixation devices 12 may also be desirable where the direction of the fracture is generally parallel to the axis of implantation as is understood in the art.

Figure 6:
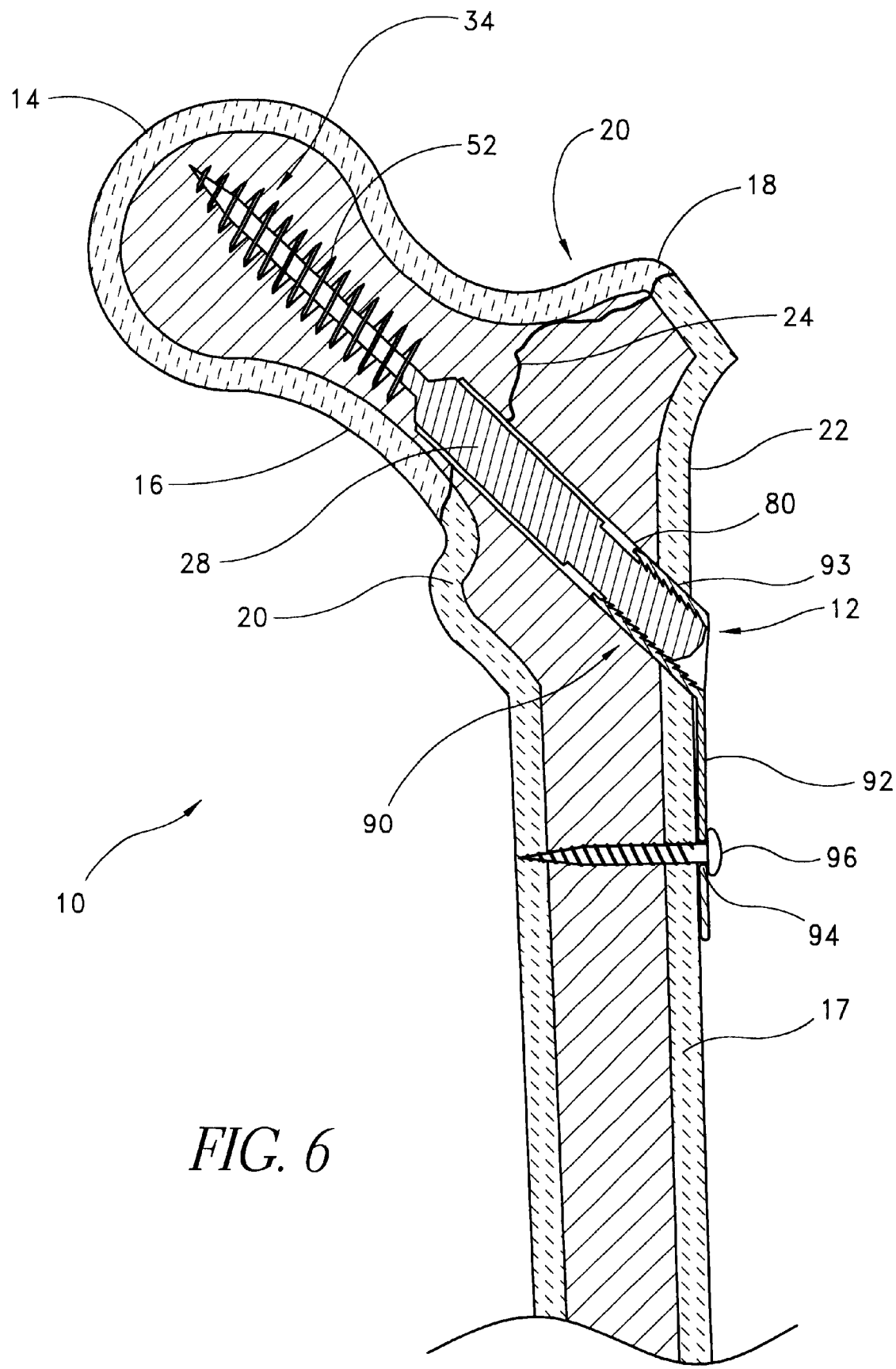
FIG. 6 is a posterior cross section as in FIG. 1, with a fixation device and integral proximal plate anchor positioned therein.

Referring to FIG. 6, there is disclosed a variation of the proximal anchor 36 in which the proximal anchor 36 is integrally formed with or attached to a plate. The fixation device 12 in FIG. 6 may otherwise be identical to the embodiments previously discussed. The proximal anchor 90 comprises an elongated flange 92, which extends from the housing 93 longitudinally down (anatomically caudad or distally) the body 17 of the femur 10. The elongated flange 80 preferably includes one or more openings 94 for receiving one or more femoral shaft screws 96. The flange 92 may or may not extend above (anatomically proximal to) the housing 93. Elimination of a proximal flange may more easily permit rotational removal of the proximal anchor 36 from the body 28 by reverse rotation in an inclined flange embodiment.

Figure 6A:
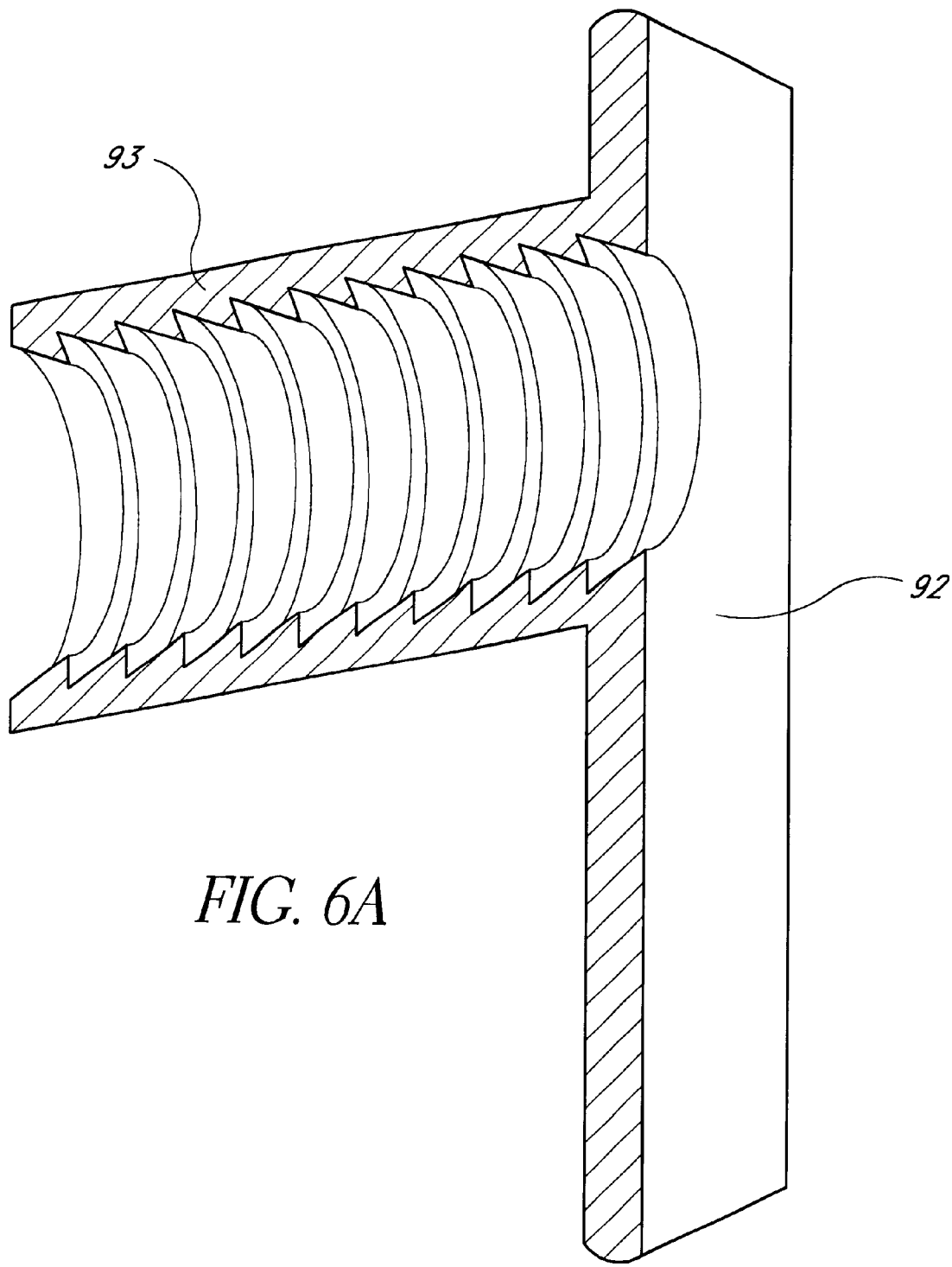
FIG. 6A is a cross sectional schematic view of a combination proximal anchor and plate in accordance with the present invention.

Referring to FIG. 6A, there is illustrated a cross sectional schematic view of an integral proximal anchor 36 and proximal plate. The dimensions and orientation of the proximal anchor 36 may be varied widely, depending upon the intended application. For example, a longitudinal axis of the housing 93 may be inclined or perpendicular with respect to the plane of flange 92. The flange 92 may have any of a variety of dimensions and profiles, depending upon the intended application. Lengths of the plate 92 in the vertical direction as illustrated on FIG. 6A, for use in femoral neck fixation fractures, may range from at least about 0.5 inches to about 10 inches or more. The plate 92 may be planar as illustrated, particularly in small plate embodiments, or may be curved or contoured to improve seating of the plate 92 against the adjacent bone. Plate 92 may be provided with one or more apertures for receiving bone screws or other fixation devices as illustrated in FIGS. 6 and 7A.

Figure 7A:
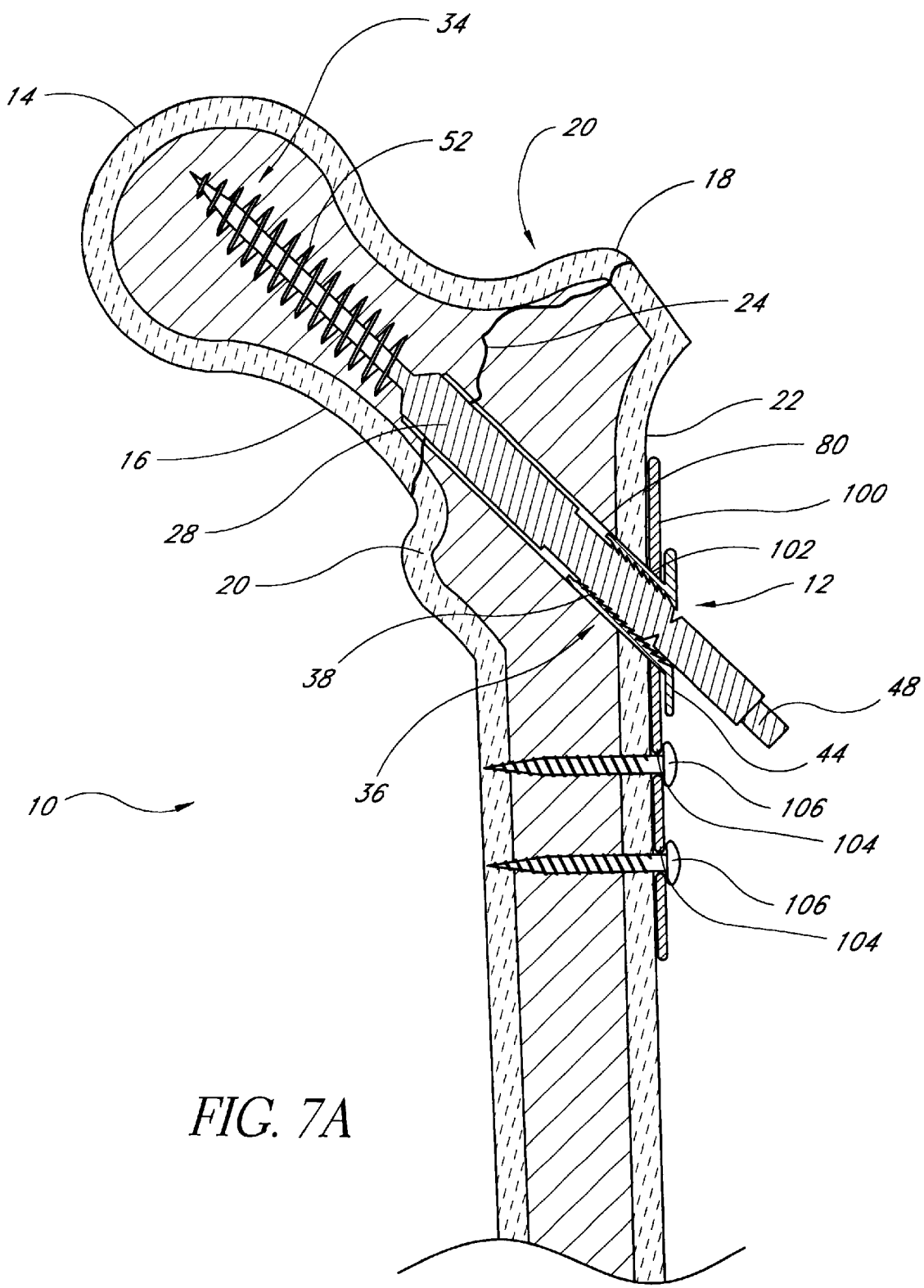
FIG. 7A is a posterior cross section as in FIG. 1, with a plate and fixation device positioned therein.
Figure 7B:
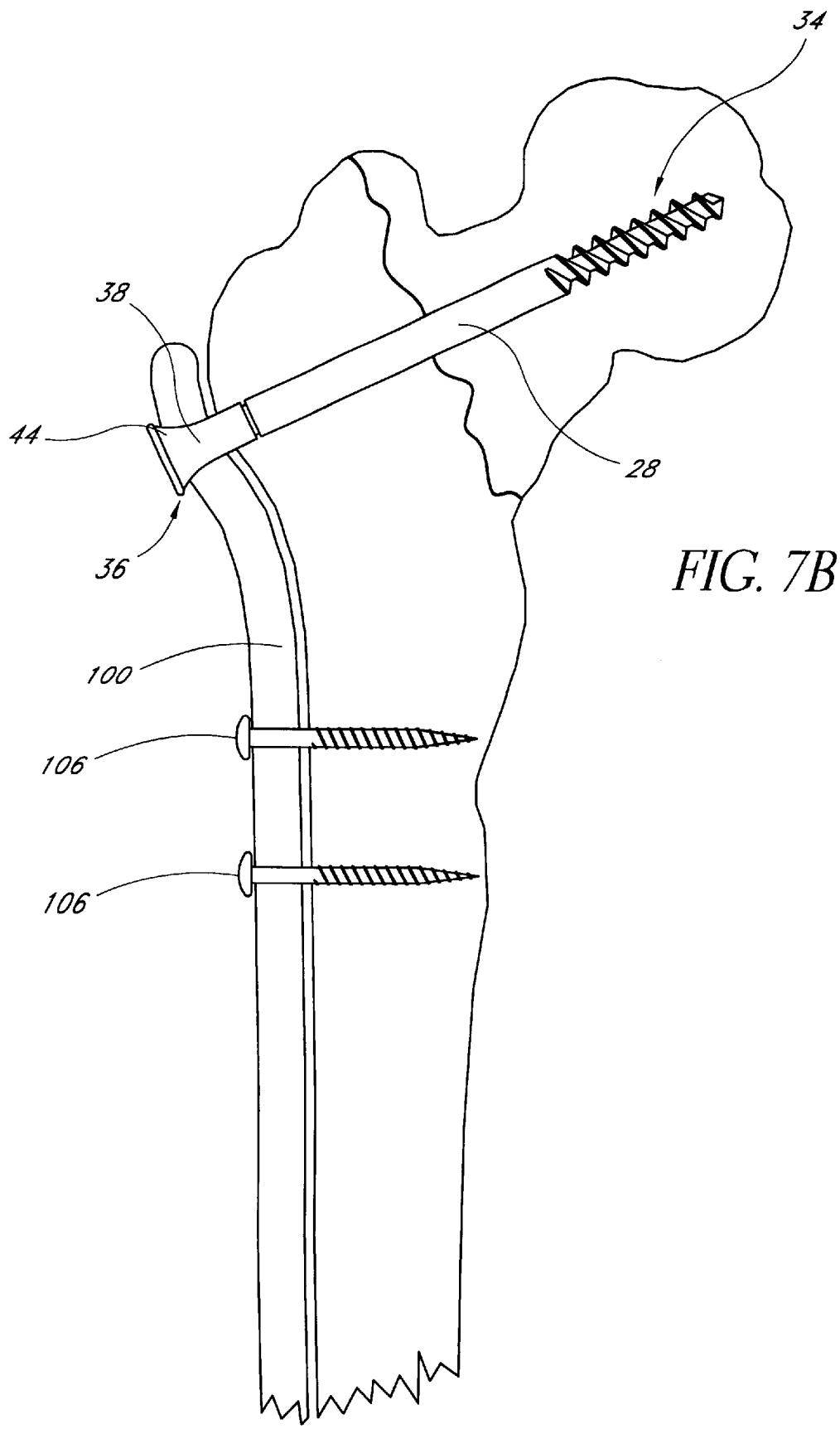
FIG. 7B is a cross section through a proximal portion of the femur, illustrating the use of a fixation device as in FIG. 4A, in combination with a plate.

Referring to FIG. 7A, the fixation device 12 is schematically illustrated in combination with a conventional plate 100. The fixation device 12 in FIG. 7A may be identical to the embodiments described elsewhere herein. The fixation device 12 is used with an elongated side plate 100, which extends longitudinally above and below the hole 80. The elongated side plate 100 includes an opening 102 that preferably has a diameter that is slightly larger than the diameter of the housing 38. The elongated side plate 100 preferably also includes one or more openings 104 for receiving one or more femoral shaft screws 106. Advantageously, the elongated side plate 100 spreads the forces exerted by the flange 44 across a larger area of the femur 17, and affects the distribution of load. In an alternate embodiment, the elongated side plate can 100 include one or more openings above the housing 38 for receiving trochanteric anchor screws (not shown). A contoured side plate 100 is illustrated in FIG. 7B.

Figure 7C:
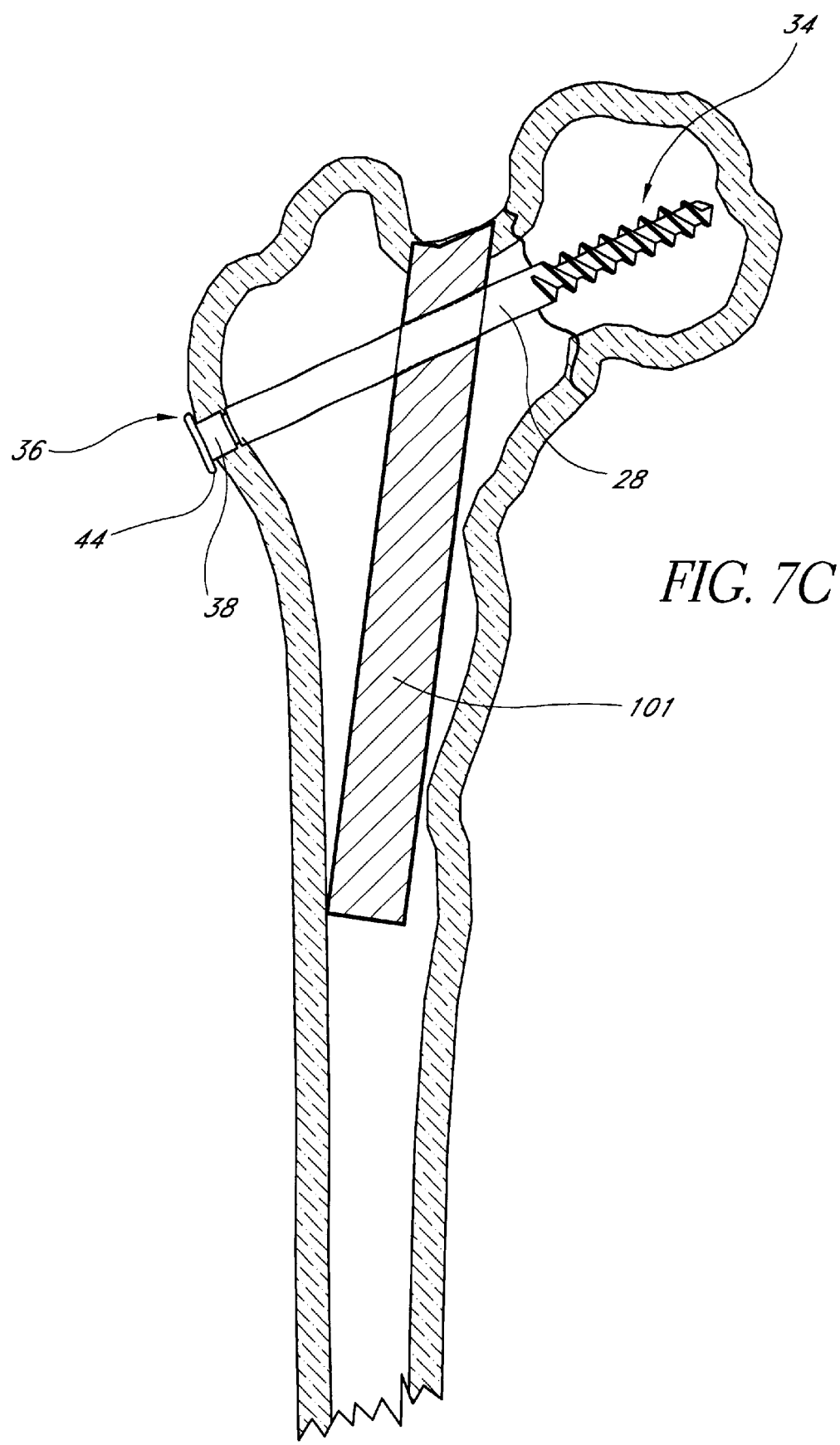
FIG. 7C is a cross section as in FIG. 7B, illustrating the use of a fixation device of the present invention in combination with an intramedullary nail.

The fixation device 12 of the present invention may also be used in combination with intramedullary nails or rods 101 as schematically illustrated in FIG. 7C, as will be understood by those of skill in the art.

Figure 10:
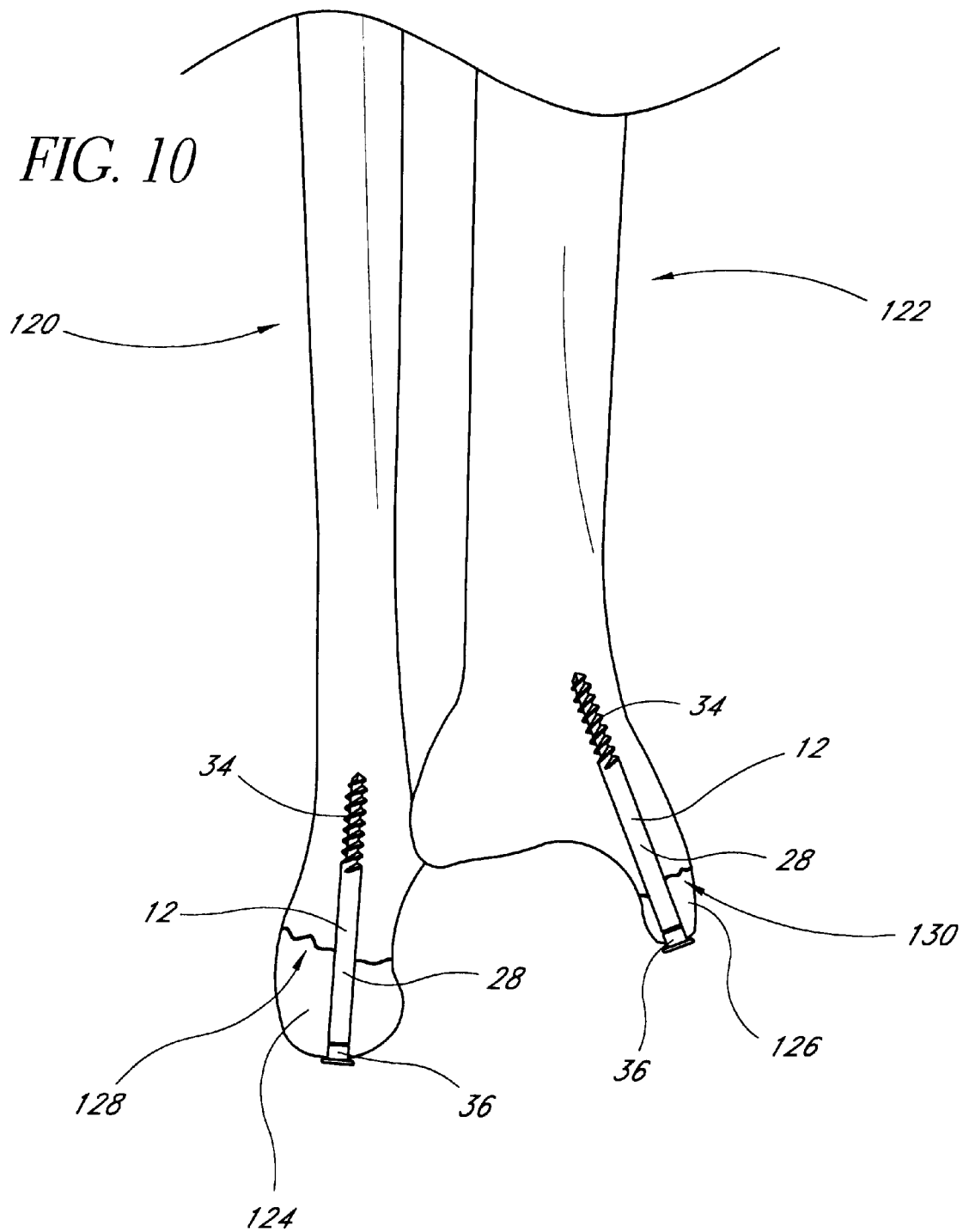
FIG. 10 is an anterior view of the distal tibia and fibula, with fixation devices across lateral and medial malleolar fractures.

The fixation device 12 of the present invention may be used in any of a wide variety of anatomical settings beside the proximal femur, as has been discussed. For example, lateral and medial malleolar fractures can be readily fixed using the device of the present invention. Referring to FIG. 10, there is illustrated an anterior view of the distal fibula 120 and tibia 122. The fibula 120 terminates distally in the lateral malleolus 124, and the tibia 122 terminates distally in the medial malleolus 126.

A fixation device 12 in accordance with the present invention is illustrated as extending through the lateral malleolus 124 across the lateral malleolar fracture 128 and into the fibula 120. Fixation device 12 includes a distal anchor 34 for fixation within the fibula 120, an elongate body 28 and a proximal anchor 36 as has been discussed.

FIG. 10 also illustrates a fixation device 12 extending through the medial malleolus 126, across a medial malleolar fracture 130, and into the tibia 122. Although FIG. 10 illustrates fixation of both a lateral malleolar fracture 128 and medial malleolar fracture 130, either fracture can occur without the other as is well understood the art. Installation of the fixation devices across malleolar fractures is accomplished utilizing the same basic steps discussed above in connection with the fixation of femoral neck fractures.

The fixation devices of the present invention may be made from either conventional bioabsorbable materials or conventional non-absorbable materials, combinations thereof and equivalents thereof. In addition, natural materials such as allografts may be used. Examples of absorbable materials include homopolymers and copolymers of lactide, glycolide, trimethylene carbonate, caprolactone, and p-dioxanone and blends thereof. The following two blends may be useful:

(1) the blend of poly(p-dioxanone) and a lactide/glycolide copolymer, as disclosed in U.S. Pat. No. 4,646,741 which is incorporated by reference.

(2) the glycolide-rich blend of two or more polymers, one polymer being a high lactide content polymer, and the other being a high glycolide content disclosed in U.S. Pat. No. 4,889,119 which is incorporated by reference.

Additional bioabsorbable materials are disclosed in copending application Ser. No. 09/558,057 filed Apr. 26, 2000, the disclosure of which is incorporated in its entirety herein by reference.

The fixation devices may also be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. Alternatively, the distal anchor comprises a bioabsorbable material, and the body and proximal anchor comprise either a bioabsorbable material or a non-absorbable material. As a further alternative, each of the distal anchor and the body comprise a non-absorbable material, connected by an absorbable link. This may be accomplished by providing a concentric fit between the distal anchor and the body, with a transverse absorbable pin extending therethrough. This embodiment will enable removal of the body following dissipation of the pin, while leaving the distal anchor within the bone.

The components of the invention (or a bioabsorbable polymeric coating layer on part or all of the anchor surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In addition, the components may be provided with any of a variety of structural modifications to accomplish various objectives, such as osteoincorporation, or more rapid or uniform absorption into the body. For example, osteoincorporation may be enhanced by providing a micropitted or otherwise textured surface on the components. Alternatively, capillary pathways may be provided throughout the body and collar, such as by manufacturing the anchor and body from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. In general, the extent to which the anchor can be permeated by capillary pathways or open cell foam passageways may be determined by balancing the desired structural integrity of the device with the desired reabsorption time, taking into account the particular strength and absorption characteristics of the desired polymer.

One open cell bioabsorbable material is described in U.S. Pat. No. 6,005,161 as a poly(hydroxy) acid in the form of an interconnecting, open-cell meshwork which duplicates the architecture of human cancellous bone from the iliac crest and possesses physical property (strength) values in excess of those demonstrated by human (mammalian) iliac crest cancellous bone. The gross structure is said to maintain physical property values at least equal to those of human, iliac crest, cancellous bone for a minimum of 90 days following implantation. The disclosure of U.S. Pat. No. 6,005,161 is incorporated by reference in its entirety herein.

The components of the present invention may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The specific dimensions of any of the bone fixation devices of the present invention can be readily varied depending upon the intended application, as will be apparent to those of skill in the art in view of the disclosure herein. Moreover, although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A femoral neck fracture fixation device, comprising:
   an elongate body, having a proximal end and a distal end;
   a helical anchor on the distal end;
   a first retention structure on the body, proximal to the anchor;
   a proximal anchor, moveably carried by the body, the proximal anchor comprising a tubular sleeve having a radially outwardly extending transverse flange; and
   a second retention structure on the interior of the tubular sleeve for cooperating with the first retention structure on the body;
   wherein the proximal anchor is movable in the distal direction with respect to the body and the retention structure resists proximal movement of the proximal anchor with respect to the body, and the flange is angularly moveable with respect to a longitudinal axis of the tubular sleeve.

2. A femoral neck fracture fixation device as in claim 1, wherein the first retention structure comprises an annular structure.

3. A femoral neck fracture fixation device as in claim 1, wherein the first retention structure comprises a flange.

4. A femoral neck fracture fixation device as in claim 1, wherein the first retention structure comprises a thread.

5. A femoral neck fracture fixation device as in claim 1, further comprising a rotational coupling on the elongate body.

6. A method of treating a femoral fracture, comprising the steps of:
   drilling a bore distally into the femur in the direction of a fracture;
   advancing a fixation device into the bore;
   rotating the fixation device to engage bone distal to the fracture; and
   advancing a proximal anchor distally along the fixation device to compress the fracture.

7. A method of treating a femoral fracture as in claim 6, wherein the drilling step comprises drilling the bore along an axis which extends through the femoral neck and into the head of the femur.

8. A method of treating a femoral fracture as in claim 6, wherein the advancing step comprises advancing a fixation device having an elongate body with a helical anchor on a distal end and a plurality of retention structures proximal to the helical anchor for engaging an axially movable proximal anchor.

9. A method of treating a femoral fracture as in claim 8, wherein the helical anchor has a major diameter within the range of from about 6 mm to about 12 mm.

10. A method of treating a femoral fracture as in claim 8, wherein the proximal anchor comprises at least one surface structure for engaging the retention structures on the elongate body.

11. A method of treating a femoral fracture as in claim 10, wherein the retention structures are spaced axially apart along the elongate body between a proximal limit and a distal limit.

12. A method of treating a femoral fracture as in claim 11, wherein the retention structures are interrupted by at least two axially extending flats.

13. A method of treating a femoral fracture as in claim 12, wherein the proximal anchor comprises a bone contacting surface which resides on a plane which is inclined at an angle within the range of from about 90 degrees to about 140 degrees with respect to the longitudinal axis of the elongate body.

14. A method of treating a femoral fracture as in claim 13, wherein the angle is about 90 degrees.

15. A method of treating a femoral fracture as in claim 13, wherein the angle is adjustable.

16. A method of treating a femoral fracture as in claim 12, wherein the proximal end of the body is provided with a rotational coupling, and additionally comprising the step of coupling a rotational driving device to the elongate body prior to the rotating step.

17. A method of treating a femoral fracture as in claim 16, wherein the rotational coupling comprises a hexagonal recess in the proximal end of the elongate body.

18. A method of treating a femoral fracture as in claim 16, wherein the drilling a bore step comprises drilling a bore having a diameter which is slightly larger than the diameter of the distal anchor.

19. A method of treating a femoral fracture as in claim 12, wherein the drilling a bore step comprises drilling a bore having a diameter within the range of from about 3 mm to about 8 mm.

20. A method of treating a femoral fracture as in claim 12, wherein the drilling a bore step comprises drilling a bore having a diameter which is slightly larger than the diameter of the distal anchor.

21. A method of treating a femoral fracture as in claim 8, wherein the fixation device has a double helix distal anchor.

22. A method of treating a femoral fracture as in claim 21, wherein the advancing a proximal anchor step comprises advancing a tubular sleeve distally along the fixation device.

23. A method of treating a femoral fracture as in claim 22, wherein the proximal anchor comprises at least one surface structure for engaging the retention structures on the elongate body.

24. A method of treating a femoral fracture as in claim 23, wherein the drilling a bore step comprises drilling a bore having a diameter which is slightly larger than the diameter of the distal anchor.

25. A method of treating a femoral fracture as in claim 23, wherein the retention structures are spaced axially apart along the elongate body between a proximal limit and a distal limit.

26. A method of treating a femoral fracture as in claim 25, wherein the retention structures are interrupted by at least two axially extending flats.

27. A method of treating a femoral fracture as in claim 26, wherein the proximal end of the elongate body is provided with a rotational coupling, and additionally comprising the step of coupling a rotational driving device to the body prior to the rotating step.

28. A method of treating a femoral fracture as in claim 27, wherein the rotational coupling comprises a hexagonal recess in the proximal end of the elongate body.

29. A method of treating a femoral fracture as in claim 8, wherein the drilling a bore step comprises drilling a bore having a diameter which is slightly larger than the diameter of the distal anchor.

30. A method of treating a femoral fracture as in claim 29, wherein the proximal anchor is carried by the fixation device prior to the advancing a fixation device step.

31. A method of treating a femoral fracture as in claim 30, further comprising the step of applying proximal traction to the elongate body during the advancing a proximal anchor distally step.

32. A method of treating a femoral fracture as in claim 30, further comprising the step of removing a proximal portion of the elongate body following the advancing a proximal anchor step.

33. A method of treating a femoral fracture as in claim 8, further comprising the steps of advancing a second fixation device into a second bore extending distally into the femur in the direction of a fracture.

34. A method of treating a femoral fracture as in claim 8, further comprising the steps of advancing the fixation device through an opening in a plate prior to the advancing a fixation device into the bore step.

35. A method of treating a femoral fracture as in claim 6, wherein the advancing a proximal anchor step comprises axially advancing the proximal anchor without rotating the proximal anchor with respect to the fixation device.

36. A method of treating a femoral fracture as in claim 35, wherein the advancing a proximal anchor step comprises advancing a tubular sleeve distally along the fixation device.

37. A method of treating a femoral fracture as in claim 36, wherein the drilling a bore step comprises drilling a bore having a diameter which is slightly larger than the diameter of the distal anchor.

38. A method of treating a femoral fracture as in claim 6, wherein the advancing a proximal anchor step comprises axially advancing the proximal anchor by rotating the proximal anchor with respect to the fixation device.

39. A method of treating a femoral fracture as in claim 6, wherein the fracture is a femoral neck fracture, an intertrochanteric fracture or a subtrochanteric fracture.

40. A method of treating a femoral fracture as in claim 6, wherein the fracture is an intertrochanteric fracture.

41. A method of treating a femoral fracture as in claim 6, wherein the fracture is a subtrochanteric fracture.

42. A method of treating a femoral fracture as in claim 6, wherein the fixation device has a length within the range of from about 45 mm to about 120 mm.

43. A method of treating a femoral fracture as in claim 6, wherein the fixation device has a diameter within the range of from about 3 mm to about 8 mm.

44. A method of treating a femoral fracture as in claim 6, wherein the anchor comprises titanium.

45. A method of securing a first bone fragment to a second bone fragment, comprising the steps of:
   drilling a bore through the first bone fragment in the direction of the second bone fragment;
   advancing a fixation device through the bore;
   rotating at least a first portion of the fixation device to secure the fixation device to the second fragment; and
   axially advancing a second portion of the fixation device to engage the first fragment.

46. A method of securing a first bone fragment to a second bone fragment as in claim 45, wherein the second bone fragment comprises the head of a femur.

47. A method of securing a first bone fragment to a second bone fragment as in claim 45, wherein the second bone fragment comprises the tibia.

48. A method of securing a first bone fragment to a second bone fragment as in claim 45, wherein the second bone fragment comprises the fibula.

49. A method of securing a first bone fragment to a second bone fragment as in claim 45, wherein the second bone fragment comprises the femur.

50. A method of securing a first bone fragment to a second bone fragment as in claim 45, wherein the first bone fragment comprises the femur.

51. A method of securing a first bone fragment to a second bone fragment as in claim 45, wherein the first bone fragment comprises a condyle.

52. A method of securing a first bone fragment to a second bone fragment as in claim 45, wherein the axially advancing step comprises rotating the second part of the fixation device about a longitudinal axis of the fixation device.

53. A method of securing a first bone fragment to a second bone fragment as in claim 45, further comprising the step of positioning a plate adjacent the first bone fragment and advancing the fixation device through the plate.

54. A method of securing a first bone fragment to a second bone fragment as in claim 45, wherein the drilling step comprises drilling a bore through the first bone fragment and into the second bone fragment.

55. A method of securing a first bone fragment to a second bone fragment as in claim 45, wherein the axially advancing a second portion step comprises advancing a tubular sleeve distally along an elongate body.

56. A method of securing a first bone fragment to a second bone fragment as in claim 55, wherein the second portion comprises at least one surface structure for engaging retention structures on the elongate body.

57. A method of securing a first bone fragment to a second bone fragment as in claim 56, wherein the drilling a bore step comprises drilling a bore having a diameter which is slightly larger than the diameter of the second portion.

58. A method of securing a first bone fragment to a second bone fragment as in claim 56, wherein the retention structures are spaced axially apart along the elongate body between a proximal limit and a distal limit.

59. A method of securing a first bone fragment to a second bone fragment as in claim 58, wherein the retention structures are interrupted by at least two axially extending flats.

60. A method of securing a first bone fragment to a second bone fragment as in claim 59, wherein the proximal end of the fixation device is provided with a rotational coupling, and additionally comprising the step of coupling a rotational driving device to the fixation device prior to the rotating step.

61. A method of securing a first bone fragment to a second bone fragment as in claim 60, wherein the rotational coupling comprises a hexagonal recess in the proximal end of the fixation device.

62. A method of securing a first bone fragment to a second bone fragment as in claim 45, wherein the a fixation device has a double helix distal anchor.

63. A method of securing a first bone fragment to a second bone fragment as in claim 62, wherein the axially advancing a second portion step comprises advancing a tubular sleeve distally along the fixation device.

64. A method of securing a first bone fragment to a second bone fragment as in claim 63, wherein the second portion comprises at least one surface structure for engaging retention structures on the fixation device.

65. A method of securing a first bone fragment to a second bone fragment as in claim 64, wherein the retention structures are spaced axially apart along an elongate body between a proximal limit and a distal limit.

66. A method of securing a first bone fragment to a second bone fragment as in claim 65, wherein the retention structures are interrupted by at least two axially extending flats.

67. A method of securing a first bone fragment to a second bone fragment as in claim 66, wherein the proximal end of the fixation device is provided with a rotational coupling, and additionally comprising the step of coupling a rotational driving device to the fixation device prior to the rotating step.

68. A method of securing a first bone fragment to a second bone fragment as in claim 67, wherein the rotational coupling comprises a hexagonal recess in the proximal end of the fixation device.

69. A method of securing a first bone fragment to a second bone fragment as in claim 45, wherein the drilling a bore step comprises drilling a bore having a diameter which is slightly larger than the diameter of a distal anchor on the first portion.

70. A method of securing a first bone fragment to a second bone fragment as in claim 69, wherein the drilling a bore step comprises drilling a bore having a diameter within the range of from about 3 mm to about 8 mm.

71. A method of securing a first bone fragment to a second bone fragment as in claim 69, wherein a proximal anchor is carried by the fixation device prior to the advancing a fixation device step.

72. A method of securing a first bone fragment to a second bone fragment as in claim 71, further comprising the step of applying proximal traction to the first portion during the advancing a second portion distally step.

73. A method of securing a first bone fragment to a second bone fragment as in claim 71, further comprising the step of removing a proximal portion of the fixation device following the advancing a second portion step.

74. A method of securing a first bone fragment to a second bone fragment as in claim 69, further comprising the steps of advancing a second fixation device into a second bore extending distally into the first bone fragment in the direction of a fracture.

75. A method of securing a first bone fragment to a second bone fragment as in claim 69, further comprising the steps of advancing the fixation device through an opening in a plate prior to the advancing a fixation device into the bore step.

76. A femoral neck fracture fixation device, comprising:
an elongate body, having a proximal end and a distal end;
a helical anchor on the distal end;
a first retention structure on the elongate body, proximal to the anchor;
a proximal anchor, moveably carried by the elongate body, the proximal anchor comprising a tubular sleeve having a radially outwardly extending transverse flange; and
a second retention structure on the interior of the tubular sleeve for cooperating with the first retention structure on the elongate body;
wherein the proximal anchor is movable in the distal direction with respect to the elongate body and the retention structure resists proximal movement of the proximal anchor with respect to the elongate body, and the flange is fixed at a non normal angle with respect to a longitudinal axis of the tubular sleeve.

77. A femoral neck fracture fixation device as in claim 76, wherein the first retention structure comprises an annular structure.

78. A femoral neck fracture fixation device as in claim 76, wherein the first retention structure comprises a flange.

79. A femoral neck fracture fixation device as in claim 76, wherein the first retention structure comprises a thread.

80. A femoral neck fracture fixation device as in claim 76, further comprising a rotational coupling on the elongate body.

* * * * *